(12) United States Patent
Zech et al.

(10) Patent No.: US 8,563,625 B2
(45) Date of Patent: *Oct. 22, 2013

(54) HYDROPHILIZED CURABLE SILICONE IMPRESSION MATERIALS WITH IMPROVED STORAGE BEHAVIOR

(71) Applicant: 3M Innovative Properties Company, St. Paul, MN (US)

(72) Inventors: Joachim Wilhelm Zech, Kaufering (DE); Rainer Guggenberger, Herrsching (DE); Henning Hoffmann, Windach (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,774

(22) Filed: Oct. 17, 2012

(65) Prior Publication Data

US 2013/0041066 A1 Feb. 14, 2013

Related U.S. Application Data

(63) Continuation of application No. 11/993,535, filed as application No. PCT/US2006/023236 on Jun. 14, 2006, now Pat. No. 8,318,831.

(30) Foreign Application Priority Data

Jun. 22, 2005 (EP) .................................. 05013474

(51) Int. Cl.
- *A61K 6/10* (2006.01)
- *A61C 9/00* (2006.01)
- *C08K 5/53* (2006.01)
- *C08G 77/12* (2006.01)

(52) U.S. Cl.
USPC ............. 523/109; 433/214; 524/126; 528/31; 528/32

(58) Field of Classification Search
USPC ............. 523/109; 524/122, 128, 126; 528/31, 528/32; 433/214

See application file for complete search history.

(56) References Cited

U.S. PATENT DOCUMENTS

| | | | |
|---|---|---|---|
| 3,188,300 A * | 6/1965 | Chalk | .............................. 528/15 |
| 3,661,744 A | 5/1972 | Kehr | |
| 3,715,334 A | 2/1973 | Karstedt | |
| 3,775,352 A | 11/1973 | Leonard | |
| 3,814,730 A | 6/1974 | Karstedt | |
| 3,933,880 A | 1/1976 | Bergstrom | |
| 4,035,453 A | 7/1977 | Hittmair | |
| 4,273,902 A | 6/1981 | Tomioka | |
| 4,657,959 A | 4/1987 | Bryan | |
| 5,677,410 A | 10/1997 | Mager | |
| 5,750,589 A | 5/1998 | Zech | |
| 5,924,600 A | 7/1999 | Keller | |
| 6,135,631 A | 10/2000 | Keller | |
| 6,239,244 B1 | 5/2001 | Stepp | |
| 6,300,455 B1 * | 10/2001 | Haselhorst et al. | ............. 528/31 |
| 6,335,413 B1 * | 1/2002 | Zech et al. | ..................... 528/32 |
| 6,346,562 B1 * | 2/2002 | Haselhorst et al. | ........... 524/106 |
| 6,762,242 B1 | 7/2004 | Del Torto | |
| 7,053,135 B2 | 5/2006 | Schaub | |
| 7,452,955 B2 | 11/2008 | Tanaka | |
| 7,968,645 B2 * | 6/2011 | Zech et al. | ..................... 524/588 |
| 8,318,831 B2 * | 11/2012 | Zech et al. | ..................... 523/109 |

FOREIGN PATENT DOCUMENTS

| | | |
|---|---|---|
| AU | 716 990 | 3/2000 |
| DE | 43 06 997 | 9/1994 |
| DE | 195 17 838 | 11/1996 |
| EP | 0 188 880 | 7/1986 |
| EP | 0 231 420 | 8/1987 |
| EP | 0 232 733 | 8/1987 |
| EP | 0 268 347 | 5/1988 |
| EP | 0 480 238 | 4/1992 |
| EP | 0 662 490 | 7/1995 |
| EP | 0 743 313 | 11/1996 |
| EP | 0 761 759 | 3/1997 |
| EP | 0 863 088 | 9/1998 |
| EP | 0 865 785 | 9/1998 |
| EP | 1 290 998 | 3/2003 |
| JP | 2002-541309 | 12/2002 |
| JP | 2004-115798 | 4/2004 |
| JP | 2006-063142 | 3/2006 |
| WO | WO 87/03001 | 5/1987 |
| WO | WO 97/37632 | 10/1997 |
| WO | WO 99/32552 | 7/1999 |
| WO | WO 2004/061003 | 7/2004 |
| WO | WO2004/098542 | * 11/2004 |

OTHER PUBLICATIONS van der Made et al., "Silane Dendrimers," *Journal of the Chemical Society, Chemical Communications*, Issue 19, pp. 1400-1401, (1992).

van der Made et al., "Dendrimeric Silanes," *Advanced Materials*, vol. 5 No. 6, pp. 466-468, (1993).

Seyferth et al., "Synthesis of an Organosilicon Dendrimer Containing 324 Si-H Bonds," *Organometallics*, 13, pp. 2682-2690, (1994).

* cited by examiner

*Primary Examiner* — Tae H Yoon
(74) *Attorney, Agent, or Firm* — Stephen L. Crooks

(57) ABSTRACT

The invention relates to hydrophilized curable silicone compositions which contain organopolysiloxanes, hydrophilizers and at least one stabilizing phosphorous compound. The compositions are particularly suitable as curable impression materials in dental applications, especially as wash impression materials.

19 Claims, No Drawings

HYDROPHILIZED CURABLE SILICONE IMPRESSION MATERIALS WITH IMPROVED STORAGE BEHAVIOR

CROSS REFERENCE TO RELATED APPLICATIONS

This application is a continuation of prior application Ser. No. 11/993,535, filed Jun. 14, 2006, now U.S. Pat. No. 8,318,831, which is a national stage filing under 35 U.S.C. 371 of PCT/US2006/023236, filed Jun. 14, 2006, which claims priority to EP Application No. 05013474.1, filed Jun. 22, 2005, the disclosures of which are incorporated by reference in their entirety herein.

FIELD OF THE INVENTION

The invention relates to hydrophilized curable silicone compositions which contain, organopolysiloxanes, hydrophilizers and at least one stabilizing phosphorous compound. The compositions are particularly suitable as curable impression materials in dental applications, especially as wash impression materials.

BACKGROUND OF THE INVENTION

Dental impression materials, e.g., VPS impression materials, are common products which dentists use to make highly precise impressions of patients' teeth. One disadvantage of some impression materials is their hydrophobic nature which may negatively impact the achievable accuracy of the detail of an impression under the moist conditions in a patients mouth. To overcome this problem, surfactants have been added to VPS impression materials to make those more hydrophilic. Many so called "hydrophilic" VPS impression materials are available in the market based on this technology.

Hydrophilicity of an impression material can be determined by a measurement of contact angles of drops of water on the surface of a sample of the impression material either in the unset or in the set phase using a standard goniometer. Generally, the higher the hydrophilicity of a VPS impression material, the lower the contact angle is. As the addition of surfactant can affect hydrophilicity, the amount of surfactant can influence the degree of hydrophilicity and the contact angle of dental materials such as VPS impression materials.

Generally, it is believed that the hydrophilicity of an impression material should be as high as possible, so there has been a tendency to develop VPS dental impression materials with increased amounts of surfactant to achieve as low contact angles as possible. However, simply increasing the amount of surfactant in a VPS impression material can cause other problems, for example, with respect to aging properties of the resulting dental materials.

Typically, VPS impression materials consist of two components—a base paste and a catalyst paste—the latter including a highly reactive platinum catalyst. These pastes are often filled into and stored in cartridges or foil bags. When a surfactant is present in the catalyst paste, interactions between the surfactant and the platinum catalyst may be observed, which are believed to retard the curing reaction and decrease the shelf life of the catalyst paste. Additionally, the properties of the cured material may be negatively influenced by such an interaction. Accordingly, it is usually necessary, to include only low amounts of surfactant, if any at all, in the catalyst paste, and to include most or all of the surfactant in the base paste.

The base paste of a VPS impression materials can also contain vinyl polysiloxanes, polysiloxanes or oligosiloxanes with Si—H-groups and additives like pigments, surfactants, plasticizers, retarders, etc. Without the presence of a platinum catalyst, the base paste should not cure because the platinum catalyst induces the hydrosilylation curing reaction of the curable components.

The retardation of curing in crosslinkable mixtures is described in U.S. Pat. No. 6,346,562 B1 and U.S. Pat. No. 6,300,455 B1. Both patents describe certain addition-crosslinkable silicone rubber systems. A generally encountered problem with such systems is, according to U.S. Pat. No. 6,346,562 B1 and U.S. Pat. No. 6,300,455 B1, that once the reactive mixture has been prepared it will cure, even at room temperature. This is particularly problematic when the production machines to make the base and catalyst pastes are not running for a relatively long time as a result of technical malfunctions or other causes. In such cases, the reactive silicone rubber mixture present in the machines can crosslink at room temperature, clogging the machines and necessitating very costly cleaning work before the machines can be restarted. For this reason, U.S. Pat. No. 6,346,562 B1 suggests the addition of at least one phosphorus compound to the reaction mixture in order to suppress curing of the mixture at room temperature. The document neither relates to hydrophilized dental materials, nor to materials designed to crosslink at room temperature.

SUMMARY OF THE INVENTION

Generally, hydrophilized dental materials should have shelf life as long as possible in order to be able to store the dental material in higher quantities, without the material losing its characteristical features with regard to material properties before and after curing.

Thus, there is a need for curable dental compositions that can be highly hydrophilized but at the same time possess good shelf life. There is also a need for a curable composition that can be highly hydrophilized, possesses good shelf life and has a curing behaviour comparable to prior art, unstabilised materials with a lower hydrophilicity.

In one aspect, the invention relates to a material which is curable at a temperature below 50° C., comprising
  (A) an organopolysiloxane composition comprising at least one organopolysiloxane (A1) with at least two ethylenically unsaturated groups per molecule as component A,
  (B) at least one organohydrogenpolysiloxane with at least 3 SiH groups per molecule as component B,
  (C) optionally organopolysiloxanes without reactive substituents as component C,
  (D) at least one hydrophilizing agent as component D,
  (E) at least one stabilizer containing at least one phosphorous atom as component E,
  (F) a catalyst for promoting the reaction between components A and B as component F,
  (G) optionally, dental additives, adjuvants and colorants as component G, and
  (H) optionally, silane compounds with at least 2 ethylenically unsaturated groups as component H.

One advantage of the invention is that the compositions of the invention have both a relatively high hydrophilicity and show no, or a relatively low level, of viscosity increase during extended storage of the compositions. Thus, if provided in the form of a multi component dental material, like an impression material, with a base paste and a catalyst paste wherein at least one of the pastes contains a relatively high amount of surfactant, the component with the high level of surfactant will not prematurely cure during extended storage. In addition to improved storage stability, some embodiments of the invention also exhibit good tear strength after curing. For example, some of the curable compositions containing organopolysiloxane provide elastomers with good tear strength upon curing and good storage stability as well as sufficient hydrophilicity that they can be used as light body or ultra light body wash materials for taking impressions, especially taking impressions within the oral cavity.

In a preferred embodiment the material according to the invention comprises:
- about 5- about 70 wt.-% components A+B+H,
- about 0- about 40 wt.-% component C,
- about 0.5- about 10 wt.-% component D,
- about 0.0001- about 0.1 wt.-% component E,
- about 0.00005- about 0.05 wt.-% component F, calculated as elemental platinum and related to the overall weight of the material present with the compounds A to H,
- about 0- about 70 wt.-% component G, and
- about 0.1- about 50 wt.-% component H.

Surprisingly, it has been found that adding a stabilizer which contains a phosphorous atom to the curable material results in an improved storage behaviour of the material while the curing behaviour and the material properties remain basically unchanged.

The invention further relates to a method of making a dental impression, wherein a material according to the invention is used.

A component A, according to the invention, contains one organopolysiloxane or a mixture of two or more polysiloxanes. In the latter case, the n polysiloxanes present in component A are named A1, A2 . . . An, respectively.

A component B, according to the invention, contains one organohydrogenpolysiloxane with at least 3 SiH groups per molecule or a mixture of two or more of such organohydrogenpolysiloxanes. In the latter case, the n organohydrogenpolysiloxanes present in component B can be named B1, B2, Bn, respectively.

A component C, according to the invention, can contain one organopolysiloxanes without reactive substituents or a mixture of two or more of such organopolysiloxanes. In the latter case, the n organopolysiloxanes present in component C can be named C1, C2, . . . Cn, respectively.

A component D, according to the invention, contains one hydrophilizing agent without reactive substituents or a mixture of two or more of such hydrophilizing agents. In the latter case, the n hydrophilizing agents present in component D can be named D1, D2, . . . Dn, respectively.

A component E, according to the invention, contains one stabilizer containing at least one phosphorous atom or a mixture of two or more of such stabilizers. In the latter case, the n stabilizers present in component E can be named E1, E2, . . . En, respectively.

A component F, according to the invention, contains a catalyst for promoting the reaction between components A and B or a mixture of two or more of such catalysts. In the latter case, the n catalysts present in component F can be named F1, F2, . . . Fn, respectively.

A component G, according to the invention, contains one or more dental additives, adjuvants or colorants or a mixture of two or more of such compounds. In the latter case, the n catalysts present in component G can be named G1, G2, . . . Gn, respectively.

A component H, according to the invention, contains one silane compound with at least 2 ethylenically unsaturated groups or a mixture of two or more of such compounds. In the latter case, the n silane compounds with at least 2 ethylenically unsaturated groups present in component H can be named H1, H2, . . . Hn, respectively.

The invention also relates to a method for the preparation of a material according to the present invention, wherein components A, B, D, E, and F and optionally one or more of components C, E and G and H are mixed.

The invention also relates to a method for the preparation of a material in a two component dosage, wherein component B and components A, D and E and one or more of components G and H are mixed to form a base paste and component F and one or more of components A, C and G and H are mixed to form a catalyst paste.

The preparation according to the invention can be performed manually or automated, especially supported by an appropriate dispensing cartridge. The present invention thus further relates to a method for the preparation of a material according to the invention using a multiple component dispensing cartridge, wherein the cartridge comprises multiple compartments and at least one compartment contains component B and components A, D and E and one or more of components G and H as a base paste and at least one other compartment contains component F and one or more of components A, C and G and H as a catalyst paste and wherein the material in the compartments is mixed upon manual or automated action upon the compartments to form a material according to the invention.

The invention further relates to a kit of parts comprising at least two containers, wherein one container comprises component B and components A, D and E and optionally one or more of components C, G and H as a base paste and at least one other container comprises component F and one or more of components A, C and G and H as a catalyst paste.

The invention further relates to the use of a curable dental impression material comprising:
(A) at least one organopolysiloxane A1 with at least two ethylenically unsaturated groups per molecule as component A,
(B) at least one organohydrogenpolysiloxane with at least 3 SiH groups per molecule as component B,
(C) optionally organopolysiloxanes without reactive substituents as component C
(D) at least one hydrophilizing agent as component D,
(E) at least one stabilizer containing at least one phosphorous atom as component E,
(F) a catalyst for promoting the reaction between A and B as component F and
(G) optionally dental additives, adjuvants and colorants as component G and
(H) optionally silane compounds with at least 2 ethylenically unsaturated groups as a component H for the preparation of impression materials in dental applications. The curable material can, e.g., comprise a mixture of component C and G or mixture of component G an H or a mixture of components C, G and H.

The invention further relates to a method for obtaining dental impressions, wherein a curable dental impression material comprising:
(A) at least one organopolysiloxane A1 with at least two ethylenically unsaturated groups per molecule as component A,
(B) at least one organohydrogenpolysiloxane with at least 3 SiH groups per molecule as component B,
(C) optionally organopolysiloxanes without reactive substituents as component C,
(D) at least one hydrophilizing agent as component D, (E) at least one stabilizer containing at least one phosphorous atom as component E, (F) a catalyst for promoting the reaction between A and B as component F and (G) optionally dental additives, adjuvants and colorants as component G and (H) optionally silane compounds with at least 2 ethylenically unsaturated groups as a component H is contacted with a region in an oral cavity of a mammal such as hard or soft dental tissue which is to be to be reproduced by an impression. The curable material can, e.g., comprise a mixture of component C and G or mixture of component G an H or a mixture of components C, G and H.

More Detailed Description of The Invention

Component A according to the invention comprises at least one organopolysiloxane A1 with at least two pendant or terminal triorganosiloxy groups in which at least one of the three organic groups is a group with an ethylenically unsaturated double bond. Generally, the groups with an ethylenically unsaturated double bond can be located on any monomeric unit of the organopolysiloxane. It is, however, preferred, that the groups with an ethylenically unsaturated double bond are located on or at least near the terminal, monomeric units of the polymer chain of the organopolysiloxane. In another preferred embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula

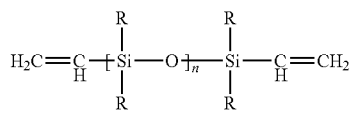

in which the radicals R, independently from each other, represent a non-substituted or substituted, monovalent hydrocarbon group with 1 to 6 C atoms, which is preferably free from aliphatic multiple bonds and where n generally can be chosen such that the viscosity of the organopolysiloxanes lies between about 4 and about 500,000 mPas or between about 6 and about 100,000 mPas. The parameter n can, e.g., be in the range of about 10 to about 3000.

Generally, the radicals R in the above formula can represent any non-substituted or substituted, monovalent hydrocarbon group with 1 to 6 C atoms. Non-substituted or substituted, monovalent hydrocarbon groups with 1 to 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction. The term "interfere" as used in the context of the present text relates to any influence of such a substituent on at least one of the other substituents or constituents of the composition or the curing reaction, or both, which is detrimental to the properties of the hardened product. The term "detrimental" as used in the context of the present text relates to a change of properties of the precursors or the cured product that negatively affect the usefulness of the precursors or the cured product in their intended use.

In another preferred embodiment of the invention, at least about 50% of the radicals R are methyl groups. Examples of other radicals R that can be present in the organopolysiloxanes according to the above formula are ethyl, propyl, isopropyl, n-butyl, tert.butyl, the pentyl isomers, the hexyl isomers, vinyl, propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially the disclosure of the latter document regarding the above mentioned molecules, their chemical constitution and their preparation, is expressly regarded as being part of the disclosure of the present document and is included herein by reference.

The preparation of molecules according to the above-mentioned formula would generally be understood by the skilled person based upon the teachings of the prior art regarding similar molecules.

Particularly preferred are linear polydimethylsiloxanes according to the above formula, that have viscosities with the specified viscosity ranges and end groups comprising dimethylvinylsiloxy units and methyl groups as the radicals R.

A component A which can be employed according to the invention can consist of one type A1 of organopolysiloxane. The organopolysiloxane can have a viscosity starting in the range of about 5 to about 500,000 mPas, or about 10 to about 50,000 mPas or about 30 to about 40,000 mPas, e.g., a viscosity of about 50 to about 20,000 mPas, or from about 100 to about 15,000 mPas or about 200 to about 10,000 mPas.

It is, however, also possible that component A comprises two or more constituents, A1, A2 and so on, which can differ, e.g., in the chemical composition of their backbone, or their molecular weight, or their substituents or their viscosity, or any other differentiating feature or two or more of the above mentioned features.

In one embodiment of the invention the difference in viscosities of different constituents of component A can be higher than a factor of 2, e.g., higher than a factor of about 5, higher than a factor of about 10, higher than a factor of about 20, higher than a factor of about 30, higher than a factor of about 40, higher than a factor of about 50, higher than a factor of about 60, higher than a factor of about 70, higher than a factor of about 80, higher than a factor of about 90 or higher than a factor of about 100. The difference in viscosities can be even higher, e.g., higher than a factor of about 200, higher than a factor of about 300, higher than a factor of about 500, higher than a factor of about 800, higher than a factor of about 1,000 or higher than a factor of about 5,000, it should, however, preferably not exceed a value higher than a factor of about 10,000. It should be kept in mind that the values mentioned above relate to a factor for the difference in viscosities, not the viscosity values themselves.

The constituent of A with the lowest viscosity of all constituents of A can have a viscosity in the range of about 10 to about 1000 mPas, or about 50 to about 500 mPas or about 100 to about 300 mPas. The constituent of A with the highest viscosity of all constituents of A can have a viscosity of about 500 to about 500,000 mPas, e.g. from about 1,000 to about 50,000 mPas or about 3,000 to about 20,000 mPas. Good results can e.g. be achieved when the constituent of A with the highest viscosity of all constituents of A has a viscosity of about 4,000 to about 15,000 mPas, e.g. from about 5,000 to about 13,000 mPas or about 6,000 to about 12,000 mPas.

In another embodiment of the invention, the component A can comprise three constituents A1, A2 and A3. In this case, if the constituents differ, e.g., in viscosity, the above mentioned definition for the relation of the viscosities of the constituent with the highest viscosity and the constituent with the lowest viscosity, A3 and A1, is also applicable. The remaining constituent A2 can generally have any viscosity with a value between the values for viscosity of A1 and A3.

A preferred method of measurement of the viscosity is performed with Haake Rotovisco RV20 (spindle MV, measuring cup NV). The viscosity is measured at 23° C. After activation and rectification of the system, spindle MV is installed. Then the material to be measured is filled into the measuring cup NV. Without undue delay, the spindle is lowered into the measuring cup NV. The spindle should be covered by a layer of the material of a maximum thickness of 1 mm. The material to be measured is tempered for 20 min at 23° C. The measurement is started by starting the spindle to turn and the viscosity values (mPas) are recorded starting 20 s after the start of measurement. Care must be exercised to ensure that the measuring cup NV does not rotate or move at any time. A value for the viscosity is obtained in mPas. The above mentioned method of measurement corresponds to DIN 53018-1.

If component A contains constituents of different viscosities, the ratio of the amount of constituent with the lowest viscosity to the amount of constituent with the highest viscosity can be chosen relatively freely, depending on the desired properties of the precursors and the cured resin. It has, however, proven to be advantageous when the ratio of the amount of constituent with the lowest viscosity to the amount of constituent with the highest viscosity is within a range of from about 1:20 to about 20:1, especially about 1:10 to about 10:1 or about 1:5 to about 5:1. Good results can e.g. be obtained with ratios of from about 1:3 to about 3:1 or about 1:2 to about 2:1. It has furthermore proven adequate in some cases, when the amount of constituent with the highest viscosity is about equal to or higher than the amount of constituent with the lowest viscosity, resulting in a value of from about 0.9:1 to about 3:1 for the ratio of the amount of constituent with the highest viscosity to the amount of constituent with the lowest viscosity. All of the ratios are based on the weight of the constituents.

Component B comprises preferably an organohydrogenpolysiloxane with at least 3 Si-bonded hydrogen atoms per molecule. By definition, an organohydrogenpolysiloxane according to the present text does not belong to the group of organopolysiloxanes as described in the context of the invention.

An organohydrogenpolysiloxane according to the invention preferably contains about 0.01 to about 1.7 wt.-% silicon-bonded hydrogens. The silicon valencies which are not saturated with hydrogen or oxygen atoms are saturated with monovalent hydrocarbon radicals R which are free from ethylenically unsaturated bonds.

The hydrocarbon radicals R, may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

Organohydrogenpolysiloxanes which can be suitable as component B or as a constituents of component B can have a viscosity of about 10 to about 1000 mPas or from about 15 to about 550 mPas or from about 20 to about 150 mPas.

Suitable compounds for use in component C are organopolysiloxanes without reactive substituents. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, $C_2$-$C_{10}$ aliphatics, trifluoropropyl groups as well as aromatic $C_6$-$C_{12}$ radicals.

Polydimethylsiloxanes with trimethylsiloxy end groups are particularly preferred as a constituent of component C. Component C is used in the material according to the invention preferably in an amount of about 0 to about 40 wt.-%, preferably about 0 to about 20 wt.-% or about 0 to about 10 wt.-%.

Hydrophilizing agents which can be employed as constituents of component D, can generally be chosen freely from all types of surfactants which improve the hydrophilicity of a silicone material which is curable via hydrosilylation reaction while at the same time do not negatively impact the material properties or curing behaviour of the material or at least not more than avoidable or tolerable. Useful surfactants which improve the hydrophilicity of a silicone material according to the invention can generally be chosen from anionic, cationic or non-ionic surfactants or mixtures of two or more of such types of surfactants.

It is preferred that the material according to the invention comprises a nonionic surfactant as a hydrophilizing agent or a mixture of two or more non-ionic surfactants.

Component D comprises an agent or a plurality of agents which are generally capable of increasing the hydrophilic character to a composition, for example as demonstrated by an increase in the wetting angle of a drop of water or an aqueous solution or dispersion (e.g. a plaster suspension or the like) on the material (in its cured or uncured state) over that wetting angle achieved on the same silicon composition without component D.

The measurement of the wetting angle to determine the hydrophilicity of impression materials is described in DE 43 06 997 A, page 5, the contents of this document with regard to this method of measurement being expressly mentioned by reference and being regarded as part of the disclosure of the present text.

Preferably, the hydrophilizing agents of component D do not contain reactive groups so that they are not incorporated into the polysiloxane network.

Ethoxylized fatty alcohols which are e.g. described in EP 0 480 238 B1 can be used as component D. Furthermore, the non-ionic perfluoroalkylated surface-active substances described in WO 87/03001 can be used. Also preferred are the non-ionic surface-active substances which are described in EP 0 268 347 B1, i.e. the nonylphenolethoxylates, polyethylene glycol-mono- and diesters, sorbitan esters as well as polyethylene glycol- mono- and diethers listed therein. The contents of the latter documents with regard to hydrophilizing agents and their preparation is expressly mentioned by reference and is regarded as part of the disclosure of the invention.

In a further embodiment of the invention, the hydrophilizing agent or at least one of the hydrophilizing agents, if component D comprises two or more hydrophilizing agents, contains silicone moieties.

Suitable hydrophilizing agents can be wetting agents from the group of hydrophilic silicone oils which are not capable of being covalently incorporated into the hardened polymer network. Suitable hydrophilizing agents are described in WO 87/03001 and in EP 0 231 420 B1, the contents of which with regard to the hydrophilizing agents are expressly mentioned by reference and are regarded as part of the disclosure of the invention.

Useful as hydrophilizing agents in component D are polyether carbosilanes of the general formula Q-P—(OC$_n$H$_{2n}$)$_x$—OT, in which Q stands for R$_3$—Si— or

where every R in the molecule can be the same or different and stands for an aliphatic C$_1$-C$_{18}$, a cycloaliphatic C$_6$-C$_{12}$ or an aromatic C$_6$-C$_{12}$ hydrocarbon radical, which can optionally be substituted by halogen atoms, R' is a C$_1$-C$_{14}$ alkylene group, R" is R in the case of a≠0 or is R or R$_3$SiR' in the case of a=0, and a=0-2; P stands for a C$_2$-C$_{18}$ alkylene group, preferably a C$_2$-C$_{14}$ alkylene group or A-R''', where A represents a C$_2$-C$_{14}$ alkylene group and R''' a functional group from the following list: —NHC(O)—, —NHC(O)—(CH$_2$)$_{n-1}$—, —NHC(O)C(O)—, —NHC(O)(CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH2)$_{n-1}$—, —OCH$_2$CH(OH)CH$_2$OC(O)(CH2)$_v$C(O)— with v=1-12; T is H or stands for a C$_1$-C$_4$ alkyl radical or a C$_1$-C$_4$ acyl radical; x stands for a number from 1 to 200 and n stands for an average number from 1 to 6, preferably 1 to 4.

The polyether part can be a homopolymer, but can also be a statistical, alternating or block copolymer.

Hydrophilizers which can be advantageously used as a part of component D or as component D, either alone or as a mixture of two or more thereof, can be found in U.S. Pat. No. 5,750,589 to Zech et al., col. 2, I. 47 to col. 3, I. 27 and col. 3, I. 49 to col. 4, I. 4 and col. 5, I. 7 to col. 14, I. 20.

Other hydrophilizers which can be advantageously used as a part of component D or as component D, either alone or as a mixture of two or more thereof, can be found in U.S. Pat. No. 4,657,959 to Bryan et al., col. 4, I. 46 to col. 6, I. 52 as well as in EP 0 231 420 B1 to Gribi et al. p4, I. 1 to p. 5, I. 16 and in the examples.

U.S. Pat. No. 5,750,589, U.S. Pat. No. 4,657,959 and EP 0 231 420 B1 are expressly described and cited herein as a source of disclosure for compounds which can be used as component D according to the invention. The documents and especially their disclosure with regard to hydrophilizers at the citations given above are incorporated by reference and are considered as being a part of the disclosure of the present text.

Further preferred surfactants are exthoxylated surfactants containing a siloxane solubilizing group as described in U.S. Pat. No. 4,657,959, the disclosure of which is incorporated herein by reference.

Suitable surfactants can have the following Formula

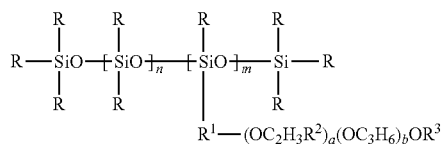

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and R$^3$ are —CH$_3$, R$^1$ is —C$_3$H$_6$—, R$^2$ is hydrogen, n is about zero or about one, m is about one to about five, a is about five to about 20 and b is about 0.

Several of such ethoxylated surfactants are available from Union Carbide Corp. as "SILWET" surface active copolymers. Preferred surface active copolymers include SILWET 35, SILWET L-77, L-7600 and L-7602. SILWET L-77 is an especially preferred ethoxylated surfactant which is believed to correspond to the above formula where R and R$^3$ are —CH$_3$, R$^1$ is —C$_3$H$_6$—, R$^2$ is hydrogen, n is about zero or about one, m is about one or about two, a is about seven, and b is about 0. Also possible is the use of MASIL® SF19, as obtainable from Lubrizol performance products, Spartanburg, US.

Also possible is the use of polyether carbosilanes selected from the group consisting of:
Et$_3$Si—(CH$_2$)$_3$—O—(C$_2$H$_4$O)$_y$—CH$_3$, Et=Ethyl
Et$_3$Si—CH$_2$—CH$_2$—O—(C$_2$H$_4$O)$_y$—CH$_3$, Et=Ethyl
(Me$_3$Si—CH$_2$)$_3$Si—(CH$_2$)$_3$—O—(C$_2$H$_4$O)$_y$—CH$_3$, Me=Methyl
Me$_3$Si—CH$_2$—SiMe$_2$-(CH$_2$)$_3$—O—(C$_2$H$_4$O)$_y$—CH$_3$, Me=Methyl
(Me$_3$Si—CH$_2$)$_2$SiMe$_2$-(CH$_2$)$_3$—O—(C$_2$H$_4$O)$_y$—CH$_3$, Me=Methyl
Me$_3$Si—(CH$_2$)$_3$—O—(C$_2$H$_4$O)$_y$—CH$_3$, Me=Methyl
Me$_3$Si—CH$_2$—CH$_2$—O—(C$_2$H$_4$O)$_y$—CH$_3$, Me=Methyl
Ph$_3$Si—(CH$_2$)$_3$—O—(C$_2$H$_4$O)$_y$—CH$_3$, Ph=phenyl
Ph$_3$Si—CH$_2$—CH$_2$—O—(C$_2$H$_4$O)$_y$—CH$_3$, Ph=phenyl
Cy$_3$Si—(CH$_2$)$_3$—O—(C$_2$H$_4$O)$_y$—CH$_3$, Cy=cyclohexyl
Cy$_3$Si—CH$_2$—CH$_2$—O—(C$_2$H$_4$O)$_y$—CH$_3$, Cy=cyclohexyl
(C$_6$H$_{13}$)$_3$Si—(CH$_2$)$_3$—O—(C$_2$H$_4$O)$_y$—CH$_3$
(C$_6$H$_{13}$)$_3$Si—CH$_2$—CH$_2$—O—(C$_4$H$_4$O)$_y$—CH$_3$ in which y conforms to the relation: 5≤y≤20.

Hydrophilizers are preferably present in the materials according to the invention in an amount of more than about 0.1% by weight, relating to the weight of the whole material. It can be preferred if the amount of component D is in a range of from about 0.1 to about 15% by weight or from about 0.3 to about 12% by weight or from about 0.5 to about 8% by weight or from about 0.8 to about 7% by weight or from about 1 to about 6% by weight or from about 1.2 to about 5% by weight or from about 1.5 to about 4% by weight.

The wetting angle of a drop of water on the surface of a cured material according to the invention measured after 10 seconds, is preferably less than about 40°, particularly preferably <about 20°, in particular <about 10°.

Wetting contact angles can be measured as follows: About 2.5 g of base and 2.5 g of catalyst paste are mixed together until uniform (about 30 s). 5 g of mixed paste is placed in a metal mould (40 mm×30 mm×2 mm) between two sheets of polyethylene and pressed flat using a glass plate. The specimen is allowed to stand undisturbed until set (about 15 minutes). The polyethylene sheets are removed, being careful not to touch the surface of the specimen, and the specimen placed on the table of a goniometer DSA 10 (Krüss), a well known device for measuring contact angles. 5 μl of water are placed onto the surface of the specimen and an automatic contact angle measurement is started using standard software of the goniometer. Measuring time is at least 10 s up to 200 s.

Component E can generally comprise any type of stabilizer containing at least one phosphorous atom, provided it does not significantly detrimentally impact the properties of the cured composition or its cure rate or any other important properties of the material according to the invention. Component E can contain one substance containing at least one phosphorous atom or a mixture of two or more substances containing at least one phosphorous atom. The stabilizer can be organic or inorganic or a mixture of organic and inorganic stabilizers can be used as component E. The stabilizer can also contain two or more phosphorous atoms.

It is particularly preferred that Component E comprises an organic stabilizer containing at least one phosphorous atom, and more particularly, an organic stabilizer selected from the group consisting of organo phosphines, organo-phosphites, organo-phosphonites, di(organo-phosphites), di(organo-phosphonites) and combinations thereof.

Also useful as compound E can be organophosphorus compounds of the formula $R^1{}_nP(OR)_{3-n}$ in which n=0, 1, 2 or 3, $R=C_1$-$C_{18}$-alkyl, $C_6$-$C_{30}$-aryl or $C_7$-$C_{31}$-alkylaryl and $R^1$=R or $(CR'_2)_m$ or $(C_6R'_4)_m$ with H=R or OR and m=10.

Especially useful can be, e.g., compounds according to the general formula $P(R)_3$, wherein R can be the same or different and $R=C_1$-$C_{18}$-alkyl, $C_6$-$C_{30}$-aryl, $C_7$-$C_{31}$-alkylaryl, or $OR^1$ with $R^1=C_1$-$C_{18}$-alkyl, $C_6$-$C_{30}$-aryl, $C_7$-$C_{31}$-alkylaryl. The radicals R or $R^1$ can be the same or different.

Moreover, representative stabilizers can have the following general formula

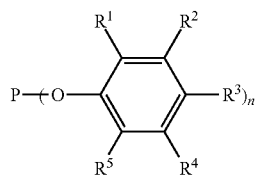

in which $R^1$, $R^2$, $R^3$, $R^4$ and $R^5$ can be the same or different and can be H, saturated or unsaturated, linear or branched C1-C18-alkyl, C6-C30-aryl or C7-C31-alkylaryl and $R^1$, $R^2$, $R^3$, $R^4$ and $R^5$ can optionally be substituted by groups such as amino, mono- or dialkylamino, carboxyl, fluorine, chlorine, bromine, cyano, benzyl, phenyl or toluoyl. Compounds which can be used as component E in the context of the invention are disclosed in U.S. Pat. No. 6,300,455 B1 to Haselhorst et al. The disclosure of this document with regard to phosphorous containing compounds and their preparation is incorporated herein by reference and its disclosure is regarded as being part of the disclosure of the present text.

If component E is chosen from the compounds according to the formula $R^1{}_nP(OR)_{3-n}$, n can be 0, 1, 2 or 3, R and $R^1$ can independently from each other be

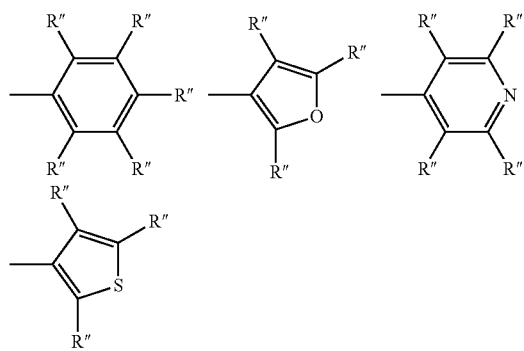

with R" independently from each other being H, $C_1$-$C_{18}$-alkyl, $C_6$-$C_{30}$-aryl or $C_7$-$C_{31}$-alkylaryl, halogen (Hal), $SiR_3$, OR and the like, especially as described in U.S. Pat. No. 6,346,562, the disclosure of this document with regard to phosphorous containing compounds and their preparation is incorporated herein by reference and the disclosure is regarded as being part of the disclosure of the present text.

Also useful as constituents of component E are diisodecylphenylphosphite (commercially available as Lankromark® LE76 by Akzo Nobel), diphenyl-2-ethylhexylphosphite (commercially available as Lankromark® LE98 by Akzo Nobel), diphenylisodecyl-phosphite (commercially available as Lankromark® LE131 by Akzo Nobel), trisnonylphenylphosphite (commercially available as Lankromark® LE109 by Akzo Nobel), tris(isodecyl)phosphate (commercially available as Lankromark® LE164 by Akzo Nobel) or tris(tridecyl)phosphate (commercially available as Lankromark® LE406 by Akzo Nobel) or mixtures of two or more of these compounds.

Particularly preferred as a constituent of component E is a compound according to the formula

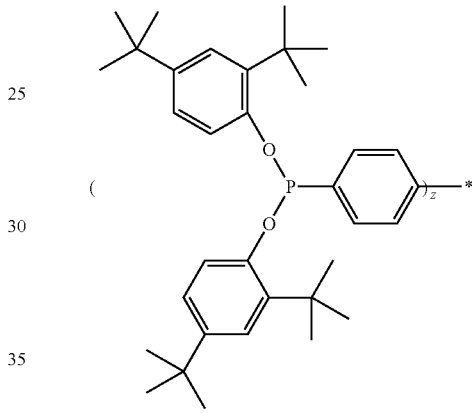

with z=2, Triphenylphosphite or Diisodecylphenylphosphite (commercially available as Lankromark LE 76® by Akzo Nobel).

The amount of Component E to be used in the material according to the invention can be within a broad range as long as the desired effect on the storage stability is achieved and side effects with regard to the material properties of the cured material or other properties of the material according to the invention are minor. It can be advantageous, if component E is present in the material according to the invention in an amount of from about 0.0001 to about 0.1% by weight, in relation to the weight of the material itself. It can, however, be preferred, if component E is present in the material according to the invention in an amount of from about 0.0005 to about 0.05% by weight, or from about 0.001 to about 0.03% by weight, in relation to the weight of the material itself.

If the material according to the invention is a multi component material, especially a material consisting of a base paste and a catalyst paste, component E is present in the base paste. It has then proven to be successful if component E is present in the base paste in an amount of from about 0.0001 to about 0.1% by weight, in relation to the weight of the material itself. It can, however, be preferred, if component E is present in the base paste in an amount of from about 0.0005 to about 0.05% by weight, or from about 0.001 to about 0.02% by weight, in relation to the weight of the material itself.

The ratio of component D to component E can be within a range of from about 10:1 to about 5000:1, especially about 30:1 to about 1000:1 or about 50 to 1 to about 600:1.

Component F preferably comprises a platinum complex which can be prepared from hexachloroplatinum acid by reduction with tetramethyldivinyldisiloxane. Such compounds are known to the skilled person. Any other platinum compounds which catalyze or accelerate addition cross-linking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable, for example. The disclosure of these patents with regard to platinum complexes and their preparation is explicitly mentioned and expressly regarded as part of the disclosure of the present text.

The platinum catalyst is preferably used in quantities of about 0.00005 to about 0.05 wt.-%, particularly about 0.0002 to about 0.04 wt.-%, each calculated as elemental platinum and related to the overall weight of the material present with the components A to G.

To control the reactivity of the addition reaction and to prevent premature curing, it may be advantageous to add an inhibitor which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the invention. Examples of such inhibitors are acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based on vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups. The inhibitor is regarded as being a part of component F.

Furthermore, the dental materials according to the invention can optionally comprise a component G, containing additives such as fillers, plasticizers, pigments, anti-oxidizing agents, release agents and the like.

For example, a chemical system may be employed to diminish the presence or degree of hydrogen outgassing which may be typically generated as a result of the vinyl polymerization. The composition thus may comprise a finely divided platinum metal that scavenges for and takes up such hydrogen. The Pt metal may be deposited upon a substantially insoluble salt having a surface area of between about 0.1 and about 40 m$^2$/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to about 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal as described e.g. in DE 29 26 405 C3 or Pd compounds as disclosed in to WO 97/37632 can be employed.

The compositions of the invention can also include a filler as component G or part of component G, e.g., a mixture of fillers. A wide variety of inorganic, hydrophilic or hydrophobic fillers may be employed such as silicas, aluminas, magnesias, titanias, inorganic salts, metallic oxides and glasses. It has been found to be possible to employ mixtures of silicon dioxides, including those derived from crystalline silicon dioxide, such as pulverized quartz (4-6 μm); amorphous silicon dioxides, such as a diatomaceous earth (4-7 μm); and silanated fumed silica, such as Cab-o-Sil TS-530 (160-240 m$^2$/g), manufactured by Cabot Corporation.

The sizes and surface areas of the foregoing materials are controlled to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or alkoxysilanes or silazanes. Such fillers can be present in amounts of from about 0 to about 65% by weight, especially about 5 to about 55 or about 20 to about 50 wt.-% of the material.

Among the fillers which can be used according to component G are fillers such as quarz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder.

Suitable fillers are also pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 μm.

The overall content of fillers is in the range from about 0 to about 90%, preferably about 30 to about 80%, with regard to components A to H.

A combination of reinforcing and non-reinforcing fillers is particularly preferred. In this respect, the quantity of reinforcing fillers ranges from about 1 to about 10 wt.-%, in particular from about 2 to about 5 wt.-%.

The difference in the named overall ranges, i.e. about 9 to about 70 wt.-%, in particular about 28 to about 55 wt.-%, is accounted for by non-reinforcing fillers.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Particularly preferred non-reinforcing fillers are quartzes, cristobalites and sodium aluminium silicates which can be surface-treated. The surface treatment can generally be carried out with the same methods as described in the case of the strengthening fillers.

The material according to the invention can also optionally contain silane compounds with at least 2 ethylenically unsaturated groups as a component H. Preferred silane compounds follow the general formula $$Si(R^1)_n(R^2)_{4-n}$$

wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms and n is 2, 3 or 4. Especially preferred radicals $R^1$ are vinyl, allyl and propargyl, especially preferred radicals $R^2$ are linear or branched $C_1$-$C_{12}$ alkyl groups. An example for a silane compound which can be used according to the present invention is tetraallylsilane, which corresponds to the above formula when $R^1$ is equal to an allyl radical and n is equal to 4.

Further preferred silane compounds follow the general formula:

wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms, a is a bivalent linear or branched or alicyclic, heterocyclic, aromatic or heteroaromatic group with 1 to about 10000 carbon atoms which can contain nitrogen or oxygen atoms and m is 2 or 3, preferably 3. Examples for bivalent radicals A are ethylene, propylene, butylene, pentylene, hexylene, heptylene, octylene, nonylene, decylene, —$H_2C$—Ar—$CH_2$—, —$C_2H_4$—Ar—$C_2H_4$— with Ar being an aromatic bivalent radical, preferably phenyl, or bivalent polyether radicals of the general type —$CH_2CH_2CH_2$—O—$[C_aH_{2a}O]_b$—$CH_2CH_2CH_2$— with and $0 \leq b \leq 2000$.

Also suitable as component H are silane dendrimers. Generally, three-dimensional, highly-ordered oligomer and polymer compounds are described as dendrimers, which are synthesized starting from small core molecules by a constantly repeating sequence of reactions. Monomer or polymer molecules with at least one reactive site are suitable as a core molecule. This is converted in a uni- or multi-level reaction with a reactant which accumulates at the reactive site of the core molecule and for its part has two new reactive sites. The conversion of core molecule and reactant yields the core cell (generation zero). By repeating the reaction, the reactive sites in the first reactant layer are converted with further reactants, again at least two new branching sites being introduced into the molecule each time (1$^{st}$ generation).

The progressive branching leads to a geometrical growth of the number of atoms for each generation. As the overall size can only grow linearly because of the number of possible covalent bonds specified by the reactants, the molecules become more tightly packed from generation to generation and they change their shape from starfish-shaped to spherical. Dendrimers of the zero and each further generation can be dendrimers used as component H according to the invention. Preferred are those of the first generation although those of much higher generations can be used.

Dendrimers of the first or higher generations are obtained as a core molecule by conversion of tri- or tetraalkenyl silanes (preferably allyl and vinyl) in a first step with hydrogenchloro-silanes. These products are converted in a further step with alkenyl-Grignard compounds.

Particularly preferred in this case are dendrimers of the first generation of the following formula:

in which $R^2$ is defined as above, n=2, 3, 4 or 5, m=0, 1, 2 or 3, and x=0 or 1.

Particularly preferred dendrimers according to this general formula are:
Me-Si((CH$_2$—CH$_2$—Si(vinyl)$_3$)$_3$
Si((CH$_2$—CH$_2$—Si(vinyl)$_3$)$_4$
Me-Si((CH$_2$—CH$_2$—CH$_2$—Si(allyl)$_3$)$_3$
Si((CH$_2$—CH$_2$—CH$_2$—Si(allyl)$_3$)$_4$
Me-Si((CH$_2$—CH$_2$—Si(allyl)$_3$)$_3$
Si((CH$_2$—CH$_2$—Si(allyl)$_3$)$_4$
Me-Si((CH$_2$—CH$_2$—CH$_2$—Si(vinyl)$_3$)$_3$
Si((CH$_2$—CH$_2$—CH$_2$—Si(vinyl)$_3$)$_4$ A. W. van der Made and P. W. N. M. van Leeuwen describe the main synthesis of those silane dendrimers in J. Chem. Soc. Commen. (1992), page 1400 and in Adv. Mater. (1993), 5, no. 6, pages 366 ff. The Synthesis begins for example with complete allylation of tetrachlorosilane to tetraallylsilane using 10% excess of allyl magnesium bromide in diethyl ether. In addition, the allyl groups are hydrosilylized with trichlorosilane in the presence of a platinum catalyst.

Finally, the conversion takes place with allyl magnesium bromide in diethyl ether. As a result, a dendrimer is obtained with 12 alkyl end groups. This first generation can also be converted to a second generation, 36 alkyl groups being obtained. The Same topic is also dealt with by D. Seyferth and D. Y Son in Organometallics (1994), 13, 2682-2690.

Conversion products of tri- or tetra- or penta- or hexa- or hepta- or octaal-kenyl(cyclo)siloxanes with hydrogenchlorosilanes are furthermore possible as a core molecule. These are converted in a further step with alkenyl-Grignard compounds and lead to dendrimers with cyclical or linear siloxane cores.

Both purified tri-, tetra-, penta-, hexa-, hepta- or octasiloxane dendrimers as well as any mixtures of those dendrimers can be used according to the Invention.

Silane dendrimers, the preparation and use as varnishes of which are known from DE 196 03 242 A1 and DE 195 17 838 A1 as well as from EP 0 743 313 A1. Dendrimers listed there are also suitable for the purpose according to the invention. Polyfunctional alkenyl compounds are furthermore suitable as cores.

Particularly suitable are trimethylolpropanetriallylether, tetrallylpentaerythrite, Santolink XI-100 (Monsanto), tetraallyloxyethane, 1,3,5-benzoltricarbonic acid triallyl ester, 1,2,4-benzoltricarbonic acid triallylester, 1,2,4,5-benzoltetracarbonic acid tetrallylester, triallyl phosphate, triallyl citrate, triallyl isocyanurate, triallyloxytriazine, hexaallylinosite, as well as general compounds which possess at least two ethylenically unsaturated groups which can be optionally substituted, for example O-allyl, N-allyl, O-vinyl, N-vinyl or p-vinylphenolether groups.

Possible polyenes are also described in U.S. Pat. No. 3,661,744 and EP 0 188 880 A1. The polyene can have e.g. the following structure: (Y)—(X)m, m being an integer greater than or equal to 2, preferably 2, 3 or 4, and X being chosen from the —[RCR]$_f$, —CR=CRR, —O—CR=CR—R, —S—CR=CR—R, —NR—CR=CR—R group, f being an integer from 1 to 9 and the R radicals having the meanings H, F, Cl, furyl, thienyl, pyridyl, phenyl and substituted phenyl, benzyl and substituted benzyl, alkyl and substituted alkyl, alkoxy and substituted alkoxy as well as cycloalkyl and substituted cycloalkyl and each being able to be the same or different. (Y) is an at least difunctional organic radical which is constructed from atoms which are chosen from the C, O, N, Cl, Br, F, P, Si and H group.

The allyl- and/or vinyl esters of the at least difunctional carbonic acids are for example very suitable polyene compounds. Suitable carbonic acids for this are those with carbon chains of 2 to 20 C atoms, preferably 5 to 15 C atoms. Allyl or vinyl esters of aromatic dicarbonic acids such as phthalic acid or trimellitic acid are also very suitable. Allyl ethers of polyfunctional alcohols, preferably at least trifunctional alcohols are also suitable. Allyl ethers of trimethyl propane, pentaerythrite triallyl ether or 2,2-bis-oxyphenylpropane-bis-(diallyl phosphate) can be named as examples. Compounds of the cyanuric acid triallylester, triallyl triazinetrione type and similar are also suitable.

Dendrimers of the above mentioned type and their preparation are described in U.S. Pat. No. 6,335,413 B1. The disclosure of this document with regard to such dendrimers and their preparation is expressly regarded as part of the disclosure of the present invention.

According to the desired properties of the dental materials, the component (H) is present in quantities of from about 0.01 to about 10 wt.-%, preferably about 0.05 to about 5 wt.-% or about 0.1 to about 1 wt.-%. Even the addition of very small amounts effects a considerable increase in the tear strength of impression materials. In a preferred embodiment, component H ist present in the dental materials in an amount of about 0.1 to about 2 wt.-%, e.g. about 0.15 to less than about 1 wt.-%.

The quantity ratios of components A, B and H are preferably chosen such that about 0.5 to about 10 mol SiH units of component B are present per mol of unsaturated double bond of components A and H. The amount of components A, H, and the B in the dental material is in the range of from about 5 to about 70 wt.-% relative to the total weight of all components. Preferably, the amount is in the range of from about 10 to about 60 wt.-% and particularly in a range of from about 15 to about 55 wt.-%.

The materials according to the invention are prepared by mixing the components A to H and subsequently curing them in an addition reaction designated as hydrosilylizing in which, under the influence of the platinum catalyst D, the SiH groups of the component B are added to the unsaturated groups of the components A and H respectively.

In a preferred embodiment the material according to the invention comprises:

about 5- about 70 wt.-% components A+B+H, about 0- about 40 wt.-% component C, about 0.5- about 10 wt.-% component D, about 0.0001- about 0.1 wt.-% component E, about 0.00005- about 0.05 wt.-% component F, calculated as elemental platinum and related to the overall weight of the material present with the compounds A to H, about 0- about 70 wt.-% component G, and about 0.1- about 50 wt.-% component H.

For reasons of storage stability, it can be preferable to formulate the materials in a two-component dosage form in which the overall component B is present in a so-called base paste. The overall component F is present physically separated from the base paste in a so-called catalyst paste. The components A or H or both can be either present in the catalyst or base paste, respectively, preferably a part of each of components A and H respectively being present in the base paste and a part of components A or H in the catalyst paste. Components C and D are present in the base paste, however, minor amounts of component D can also be present in the catalyst paste as long as the amount is sufficiently small not to interfere with the curing ability of the catalyst.

The invention thus also relates to a material, wherein said material is present in the form of a base paste and a catalyst paste physically separated from it. The whole component B should be present in the base paste and the whole component F should be present in the catalyst paste. Preferably at least a majority of component D and at least a majority of component E should be present in the base paste, preferably more than about 90% by weight or more, e.g., more than about 95, about 98, about 99 or even about 100% by weight of components D and E should be present in the base paste. The remaining components can be optionally distributed in the two pastes.

The volume ratios of catalyst and base pastes can be about 10:1 to about 1:10. A particularly preferred volume ratio of base paste:catalyst paste is about 1:1. In the case of a volume ratio of about 1:1, the components A to H can be distributed as follows as base and catalyst paste.

TABLE 1

| Component | Base paste (wt.-%) | Catalyst paste (wt.-%) | Total in base and catalyst paste (wt.-%) |
|---|---|---|---|
| (A) | 10-60 | 10-60 | 10-60 |
| (B) | 2-60 | — | 1-30 |
| (C) | 0-20 | 0-20 | 0-20 |
| (D) | 0.1-10 | 0-10 | 0.05-10 |
| (E) | 0.001-0.05 | — | 0.0005-0.025 |
| (F) | — | 0.00025-0.25 | 0.00005-0.05 |
| (G) | 0-70 | 0-70 | 0-70 |
| (H) | 0-20 | 0-20 | 0-20 |

Preferred quantity ratios can be used as follows:

TABLE 2

| Component | Base paste (wt-%) | Catalyst paste (wt.-%) | Total in base and catalyst paste (wt.-%) |
|---|---|---|---|
| (A) | 20-55 | 20-55 | 20-55 |
| (B) | 5-20 | — | 2.5-10 |
| (C) | 0-10 | 0-10 | 0-10 |
| (D) | 0.5-5 | 0-5 | 0.25-5 |
| (E) | 0.005-0.03 | — | 0.0025-0.015 |
| (F) | — | 0.005-0.1 | 0.0025-0.05 |
| (G) | 20-60 | 30-65 | 25-62.5 |
| (H) | 0-5 | 0-5 | 0-5 |

The base paste and catalyst paste can also be used in a ration of 5:1. With a volume ratio 5:1, both pastes can be filled into tubular film bags and later, shortly before use, can be mixed using a mixing and dosing device such as PENTA-MIX™ (3M ESPE). A dosage in the form of double-chambered cartridges or capsules is also possible. Suitable devices are, e.g., described in EP 0 232 733 A1, U.S. Pat. No. 5,924,600, U.S. Pat. No. 6,135,631 and EP 0 863 088 A1, The cited documents are expressly mentioned as sources of disclosure for delivery and handling devices such as film bags, mixing and dosing devices. The cited documents are incorporated into the present text by reference and are the disclosure of the documents with regard to delivery and handling devices usable for curable materials according to the present invention is regarded as being a part of the disclosure of the present text.

The compounds according to the present invention are generally obtainable by mixing the respective components in the amounts given above. Generally, the mixing of the components can be performed manually, e.g., by spatula or a manually operated multi compartment dispenser, or automated, using one of the various available devices available for such an automated task, preferably one of the devices mentioned in EP 0 232 733 A1, U.S. Pat. No. 5,924,600, U.S. Pat. No. 6,135,631 or EP 0 863 088 A1.

The materials according to the invention are particularly suitable as dental materials, especially as dental impression materials such as precision impression materials, situation impression materials, bite impression materials.

The materials of the invention preferably have tear strengths between about 2.1 and about 8 MPa, and more preferably between about 2.4 and about 5 MPa. It has, however, been found to be advantageous in some situations, if the tear strength does not exceed a value greater than about 15 MPa. Generally, compositions with tear strength values between about 2.1 and about 6 MPa, and especially between about 2.4 and about 5 MPa, allow easy removability of the cured and imprinted material from the mouth without compromising details of the impression preparation.

The Materials according to the invention preferably have shore hardness A values greater than or equal to about 40, preferably greater than or equal to about 45, and particularly preferably greater than or equal to about 50 with low processing viscosity and non-dripping consistency according to ISO 4823. The upper limit for the shore A hardness of the cured materials according to the invention can be at a value of about 70, or about 65.

The materials according to the invention exhibit an improved elasticity, measurable by an elongation of at least about 50%, preferably of at least about 70%. Preferably the elongation of the materials according to the invention is larger than about 100%, preferably larger than about 200%.

It is also a preferred feature of the materials according to the invention that their consistency according to ISO 4823 is either in the range as described for heavy body materials, which is from about 25 to about 35 or is in the range as described for light body materials, which is greater than about 36 mm, preferably greater than about 37 mm or greater than about 38 mm or greater than about 40 mm. Most preferred materials according to the invention exhibit a consistency of more than about 41 mm, e.g., between about 42 and about 48 mm. The upper limit for the consistency according to ISO 4823 can be about 55 mm.

The invention is explained in further detail by the following examples.

EXAMPLES

1. Materials

1.1 Example A

Base Paste According to the Invention

| Compound | Amount [%-weight] |
|---|---|
| Vinyl-terminated Polydimethylsiloxanes, 4000 cSt | 46.000 |
| Polymethylhydrogensiloxanes | 12.000 |
| Polydimethylsiloxane | 5.995 |
| Hydrophobized fumed silica (100 m$^2$/g) | 4.000 |
| Hydrophobized SiO$_2$ filler | 30.500 |
| Triphenylphosphite | 0.005 |
| Carbosilane Surfactant | 1.500 |

1.2 Example B

Catalyst Pate

| Compound | Amount [%-weight] |
|---|---|
| Vinyl-terminated Polydimethylsiloxane, 2000 cSt | 39.200 |
| Polydimethylsiloxane | 5.500 |
| SiO$_2$ filler | 50.000 |
| Hydrophobized fumed silica (100 m$^2$/g) | 3.100 |
| Tetraallylsilane | 0.500 |
| Palladiumchloride Dispersion in silicone oil | 0.100 |
| Platinum catalyst solution | 1.600 |

1.3 Example C

Comparative Base Paste not According to the Invention

| Compound | Amount [%-weight] |
|---|---|
| Vinyl-terminated Polydimethylsiloxane, 4000 cSt | 46.000 |
| Polymethylhydrogensiloxane | 12.000 |
| Polydimethylsiloxane | 6.000 |
| Hydrophobized fumed silica (100 m$^2$/g) | 4.000 |
| Hydrophobized SiO$_2$ filler | 30.500 |
| Carbosilane Surfactant | 1.500 |

2. Measurements

Tear Strength:

Tear strength data were evaluated by tearing six I-shaped specimens with a central unit of 20 mm×4 mm×2 mm in a Zwick 1435 Universal testing machine according to DIN 53504. The diameter of the samples was 6 mm and their length 50 mm. Base and catalyst pastes were mixed through a static mixer and filled into a brass mold. After 24 hours at 23° C. the specimen were removed, six measurements were made and the mean value determined (speed 200 mm/min).

Setting Times:

Setting time data are given for room temperature and evaluated using a Shawbury Curometer. The end of the setting time was defined as the time after with the curing curve fell below the 10 mm line.

Shore hardness according to DIN 53505.

3. Properties

The following examples show that the effect of the stabilizer Triphenylphosphite in Example A on the curing reaction of the mixture of base and catalyst paste and on the properties of the set rubber compared to the comparative example (Base Paste Example C).

| Combination | | Tear | Shore Hard- | Setting time | |
|---|---|---|---|---|---|
| Base pate | Catalyst pate | Strength (24 h) [MPa] | ness A 10 min/24 h | at 23.0° C. [min] | Consistency [mm] |
| Example A | Example B | 2.75 | 52/58 | 5.17 | 45 |
| Example C | Example B | 2.67 | 53/58 | 5.92 | 45 |

4. Aging Studies

4.1 Viscosities of Examples

In the following examples base and catalyst pastes were filled into typical two-chambered cartridges. Those were stored at elevated temperatures. After certain periods of storage at 70° C. and 50° C. the cartridges were re-examined. The data show the viscosities of the base paste side of the cartridges.

Storage at 70° C.

|  | Inventive Combination | | Comparison Combination | |
| --- | --- | --- | --- | --- |
|  | Base Paste Example A | Catalyst Paste Example B | Base Paste Example C | Catalyst Paste Example B |
| Start | 9 Pas | | 9 Pas | |
| 1 Week | 8 Pas | | polymerised | |
| 1 Month | 8 Pas | | | |
| 3 Months | polymerised | | | |

Storage at 50° C.

|  | Inventive Combination | | Comparison Combination | |
| --- | --- | --- | --- | --- |
|  | Base Paste Example A | Catalyst Paste Example B | Base Paste Example C | Catalyst Paste Example B |
| Start | 9 Pas | | 9 Pas | |
| 1 Week | 9 Pas | | 13 Pas | |
| 1 Month | 9 Pas | | 48 Pas | |
| 3 Months | 8 Pas | | Polymerised | |
| 6 Months | 11 Pas | | | |
| 9 Months | 15 Pas | | | |
| 12 Months | 12 Pas | | | |
| 18 Months | 14 Pas | | | |
| 24 Months | 17 Pas | | | |

These results show the effect of the organophosphorus compound on the viscosity of the base paste. At 50° C. even after 2 years there was no preliminary polymerization of the base paste whereas the comparative example showed a polymerization of the base paste in the cartridge after only 3 months.

4.2 Stabiliser Tests

A solution consisting of the following components was produced to perform stabilization tests:

| Component | Amount [%] |
| --- | --- |
| Vinyl-terminated Polydimethylsiloxane, 200 cSt | 82.1% |
| Polymethylhydrogensiloxane | 16.4% |
| Carbosilane Surfactant | 1.47% |

To this basic solution, stabilisers were added and the solution was stirred for 30 min. Then the test was stored in open glass beakers for 16 h at 80° C.

Results:

| Stabiliser | Result |
| --- | --- |
| None | Polymerised |
| 100 ppm Divinyltetramethyldisiloxane | Polymerised |
| 50 ppm Ionol | Polymerised |
| 100 ppm Ionol | Polymerised |
| 250 ppm Ionol | Polymerised |
| 0.8% Vitamin E | Polymerised |
| 100 ppm Lankromark LE 76 | No Viscosity Change |
| 100 ppm Triphenylphosphite | No Viscosity Change |

These model experiments show the effect of organophosphorus compounds on the stability of reactive systems including a surfactant compared to other curing retarders or antioxidants.

What is claimed is:

1. Kit of parts for preparing a dental impression material which is curable at a temperature below 50° C., the kit comprising at least two containers, wherein one container is a base paste container that contains a base paste comprising:
   (A) at least one organopolysiloxane A1 with at least two ethylenically unsaturated groups per molecule as component A,
   (B) at least one organohydrogenpolysiloxane with at least 3 SiH groups per molecule as component B,
   (D) at least one hydrophilizing agent as component D,
   (E) at least one stabilizer containing at least one phosphorous atom as component E, and at least one other container is a catalyst paste container that contains a catalyst paste comprising:
   (A) at least one organopolysiloxane A1 with at least two ethylenically unsaturated groups per molecule as component A, and
   (F) a catalyst for promoting the reaction between A and B as component F.

2. The kit of claim 1, wherein the hydrophilizing agent is a surfactant.

3. The kit of claim 2, wherein the surfactant is a non-ionic surfactant.

4. The kit of claim 1, wherein the hydrophilizing agent contains silicone moieties.

5. The kit of claim 1, wherein the stabilizer is a compound of the formula $R^1{}_nP(OR)_{3-n}$, n is 1, 2 or 3, R and $R^1$ can independently from each other be

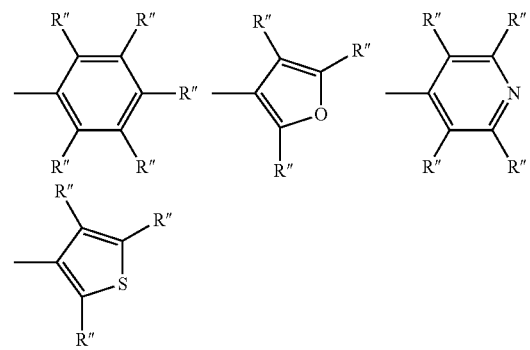

with R″ independently from each other being H, $C_1$-$C_{18}$-alkyl, $C_6$-$C_{30}$-aryl or $C_7$-$C_{31}$-alkylaryl, halogen (Hal), or $SiR_3$.

6. The kit of claim 5, wherein the stabilizer is a triarylphosphite.

7. The kit of claim 6, wherein the stabilizer is triphenylphosphite.

8. The kit of claim 5, wherein the stabilizer is diisodecylphenylphosphite.

9. The kit of claim 1, wherein the stabilizer is a compound of the formula

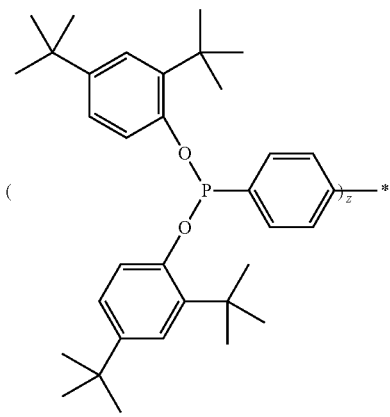

with z=2.

10. The kit according to claim 1, wherein the kit further comprises at least one of:
(C) organopolysiloxanes without reactive substituents as component C or
(G) dental additives, adjuvants and/or colorants as component G or
(H) silane compounds with at least 2 ethylenically unsaturated groups as component H,
wherein components C, G, and H, when present, are optionally distributed in the base paste and the catalyst paste.

11. The kit according to claim 1, wherein said kit further comprises component H,
wherein component H comprises a silane of the following formula:

$Si(R^1)_n(R^2)_{4-n}$ wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms and n is 2, 3 or 4, or
wherein component H comprises a silane compound of the general formula:

$(R^1)_m(R^2)_{3-m}Si\text{-}A\text{-}Si\text{---}(R^1)_m(R^2)_{3-m}$ wherein $R^1$ and $R^2$ are independently from each other defined as above, A is a bivalent linear or branched or alicyclic, heterocyclic, aromatic or heteroaromatic group with 1 to 10000 carbon atoms which can contain nitrogen or oxygen atoms and m is 2 or 3, or
wherein component H comprises a dendrimer of the following formula $SiR^2_x((CH_2)_n\text{---}Si\text{---}((CH_2)_m\text{---}CH\text{=}CH_2)_3)_{4-x}$ in which $R^2$ is defined as above, n=2, 3, 4 or 5, m=0, 1, 2 or 3, and x=0 or 1.

12. The kit according to claim 1, wherein the volume ratio of base paste to catalyst paste is 10:1 to 1:10.

13. A method of preparing a dental impression material, the method comprising:
providing a kit according to claim 1; and
mixing the base paste of the kit according to claim 1 with the catalyst paste of the kit according to claim 1 to obtain the dental impression material.

14. The method of claim 13, wherein the dental impression material has a consistency value according to ISO 4823 in a range from about 25 mm to about 35 mm.

15. The method of claim 13, wherein the dental impression material has a consistency value according to ISO 4823 of greater than 36 mm.

16. The method of claim 13, wherein the dental impression material has a Shore hardness A value in a range from about 40 to about 70.

17. The method of claim 13, wherein the dental impression material has a setting time at 23.0° C. in a range of about 5 minutes to about 6 minutes.

18. The method of claim 13, wherein the dental impression material has a tear strength value in a range from about 2.1 MPa to about 6 MPa.

19. The method of claim 13, wherein the base paste container and the catalyst paste container are each a film bag or are each one of two chambers in a double chamber cartridge.

* * * * *

UNITED STATES PATENT AND TRADEMARK OFFICE
CERTIFICATE OF CORRECTION

PATENT NO. : 8,563,625 B2  
APPLICATION NO. : 13/653774  
DATED : October 22, 2013  
INVENTOR(S) : Joachim Zech Page 1 of 2

It is certified that error appears in the above-identified patent and that said Letters Patent is hereby corrected as shown below:

Specification

<u>Column 1</u>
Line 9, Delete "Jun. 14, 2006," and insert -- Mar. 31, 2010, --, therefor.

<u>Column 4</u>
Line 55, Delete "G an H" and insert -- G and H --, therefor.

<u>Column 5</u>
Line 12, Delete "G an" and insert -- G and --, therefor.

<u>Column 6</u>
Line 5, Delete "tert.butyl," and insert -- tertbutyl, --, therefor.

<u>Column 9</u>
Line 47, Delete "exthoxylated" and insert -- ethoxylated --, therefor.

<u>Column 11</u>
Line 10, Delete "organo phosphines," and insert -- organo-phosphines, --, therefor.

<u>Column 11</u>
Line 40, Delete "toluoyl." and insert -- toluyl. --, therefor.

<u>Column 14</u>
Line 14, Delete "quarz," and insert -- quartz, --, therefor.

<u>Column 16</u>
Line 9, Delete "alkyl" and insert -- allyl --, therefor.
Line 10, Delete "alkyl" and insert -- allyl --, therefor.

Signed and Sealed this
First Day of July, 2014

Michelle K. Lee
*Deputy Director of the United States Patent and Trademark Office*

Specification Con't

Column 17
Line 7, Delete "ist" and insert -- is --, therefor.

Column 18
Line 30, Delete "ration" and insert -- ratio --, therefor.

Column 19
Line 50, Delete "Pate" and insert -- Paste --, therefor.

Column 20
Line 59 (approx), Delete "Pate" and insert -- Paste --, therefor.
Line 59 (approx), Delete "Pate" and insert -- Paste --, therefor.